United States Patent [19]

Scott et al.

[11] Patent Number: 4,691,699
[45] Date of Patent: Sep. 8, 1987

[54] ORTHOPEDIC CAST SPACING AND SPREADING DEVICE

[76] Inventors: James W. Scott, P.O. Box 7630, Tifton, Ga. 31794; John Hickox, 400 Northfield Rd., Valdosta, Ga. 31602

[21] Appl. No.: 849,715

[22] Filed: Apr. 9, 1986

[51] Int. Cl.[4] .............................................. A61F 5/04
[52] U.S. Cl. .................................. 128/91 A; 128/83; 128/91 R
[58] Field of Search ............. 128/83, 90, 91 R, 91 A; 446/85, 117, 124

[56] References Cited

U.S. PATENT DOCUMENTS

| | | | |
|---|---|---|---|
| 2,519,520 | 8/1950 | Waxlax | 128/91 A |
| 2,757,666 | 9/1956 | Grant. | |
| 3,085,569 | 4/1963 | Cook et al. | 128/91 R |
| 3,426,752 | 2/1969 | Laico. | |
| 3,631,855 | 1/1972 | Fehlau | 128/91 A X |
| 3,643,657 | 2/1972 | Whyte | 128/91 R |
| 3,957,237 | 5/1976 | Campbell | 248/317 |
| 3,998,220 | 12/1976 | Cleer, Jr. et al. | 128/91 R |
| 4,069,991 | 1/1978 | Savnders et al. | 248/317 |
| 4,129,127 | 12/1978 | Ellison | 128/91 R X |
| 4,372,300 | 2/1983 | Drennan et al. | |

FOREIGN PATENT DOCUMENTS 0467839 12/1951 Italy .................................. 446/124

Primary Examiner—Robert A. Hafer
Assistant Examiner—Kathleen J. D'Arrigo
Attorney, Agent, or Firm—Bradford E. Kile

[57] ABSTRACT

An orthopedic cast spacing and spreading device including a first othogonal member having one end face and mutually parallel sidewall surfaces and a second orthogonal member having a generally planar end face and mutually sidewall surfaces. The other ends of the first and second orthogonal members are coaxially joined and at least one flange laterally projects from said orthopedic cast spacing and spreading device at the junction of said first and second orthogonal members. A physician may selectively insert either said first orthogonal member or said second orthogonal member into a kerf formed in a patient's cast to relieve pressure created by the cast in the event of swelling of patient's limb.

8 Claims, 8 Drawing Figures

ORTHOPEDIC CAST SPACING AND SPREADING DEVICE

BACKGROUND AND FIELD OF INVENTION

The subject invention relates to a device for use by orthopedic physicians or surgeons in connection with patient bone fracture and ligament management. More particularly, the invention relates to a novel orthopedic cast spacing and spreading device operable to relieve pressure in connection with the use of an immobilizing cast structure.

When a patient fractures an arm or a leg, or damages a ligament to the point that casting is indicated, it is important to insure relative immobility of the member. Accordingly, cast materials are designed to be rigid and do not permit deformation or play in the damaged member.

If the soft body tissue of an arm or leg which has been traumatized during an injury, severe enough to fracture a bone and/or damage a joint, swells from the injury within a confined space created by a cast, post casting pressure can cause skin erosion or sores. If such pressure is permitted to persist in muscle compartments, it is possible to actually cause death of the muscle and damage to arteries and/or nerves. This is commonly referred to as compartment syndrome and most references and literature refer to it as "Volkmann" disease and contractures. Contractures can result in a significant loss of function of an extremity as well as shortening and cosmetic deformities.

In the past, if a surgeon or physician suspected that an extremity was swelling within a cast, the cast was often completely removed and a new cast applied. In many situations, however, it is preferable to simply use a saw to longitudinally cut the cast material and temporarily spread the cast to relieve pressure due to internal swelling. When swelling subsided, the cast could be closed back around the member and rebound with a top layer of plaster cloth.

A cast spreader device which has previously been known in the art is depicted in a U.S. Pat. No. 3,426,752. The disclosure of this cast spreader instrument is hereby incorporated by reference as though set forth at length for purposes of disclosing the background of the instant invention. Another cast spreader device is disclosed in U.S. Pat. No. 2,757,666. The disclosure of this cast spreader device is also incorporated by reference to further illustrate cast spreading devices existing in the prior art.

With conventional plaster cast materials, a cast spreading tool, such as identified above, could be used to separate the cast and the plaster material would remain in a separated or open posture without tending to collapse back to its original configuration. With newer fiber glass and resin materials, however, a physician can spread a cast but as soon as the separating instrument is removed from between the two sides of the cast, the cast to its original configuration tightly around a patient's limb.

Although it has been known, as an expedient, to insert bits of tape or rubber stoppers from syringes into the kerf of a spread apart cast, problems exist with this procedure. More specifically, there is no standard width with such devices and no reliability that pressure on the body member will be relieved. Moreover, such expedient structures have a tendency to fall into a kerf of the cast creating local skin necrosis or further damage.

The difficulties suggested in the proceeding are not intended to be exhaustive, but rather are among many which illustrate a need for a device for uniformly providing spacing capability for an orthopedic cast. Other noteworthy problems may also exist, however, those presented above should be sufficient to demonstrate that devices to facilitate orthopedic cast management will admit to worthwhile improvement.

OBJECTS OF THE INVENTION

It is therefore a general object of the invention to provide a novel orthopedic cast spacing and spreading device which will obviate or minimize difficulties of the type previously described.

It is a specific object of the invention to provide an orthopedic cast spacing and spreading device which will provide a capability to select a plurality space dimensions with a single unit or structure.

It is another object of the invention to provide a novel orthopedic cast spacing and spreading device which will obviate or minimize any tendency of the device to slip or fall into an open kerf of a separated orthopedic cast.

It is a further object of the invention to provide a novel orthopedic cast spacing and spreading device which has the capability of being secured in a designated location.

It is still a further object of the invention to provide a novel orthopedic cast spacing and spreading device wherein penetration of the device into the kerf of a longitudinally cut cast is limited to prevent irritating contact with a patient's skin.

It is yet a further object of the invention to provide a novel orthopedic cast spacing device which may be uniformly manufactured as a single unit with nonmoveable parts to permit wide and economical utilization.

It is another object of the invention to provide a novel orthopedic cast spacing and spreading device which will effect any combination of the foregoing objects.

BRIEF SUMMARY OF A PREFERRED EMBODIMENT

An orthopedic cast spacer and spreading device in accordance with a preferred embodiment of the invention includes a first orthogonal member having planar sidewalls and perpendicular end faces. A second orthogonal member having generally planar sidewalls and perpendicular end faces is joined to an end face of the first orthogonal member. At the junction of the first and second orthogonal members, a transverse or laterally extending flange is provided and the first orthogonal member is dimensionally larger than the second orthogonal member.

With a device of the type described above, an orthopedic physician may selectively insert either the first or second orthogonal member into a longitudinal kerf cut into a patients orthopedic cast to maintain the spacing or spreading of the kerf in the cast. The lateral flanges operably rests upon an outer surface of the cast and prevents the device from falling into the kerf and further permits a physician to immobilize the spacing and spreading device by applying adhesive tape over the device to bind the device to the cast.

DETAILED DESCRIPTION

Operative Context of the Invention

Prior to providing a detailed description of a preferred embodiment of the subject invention, it may be worthwhile to briefly establish the operative context in which the subject invention is utilized.

Figure 1:
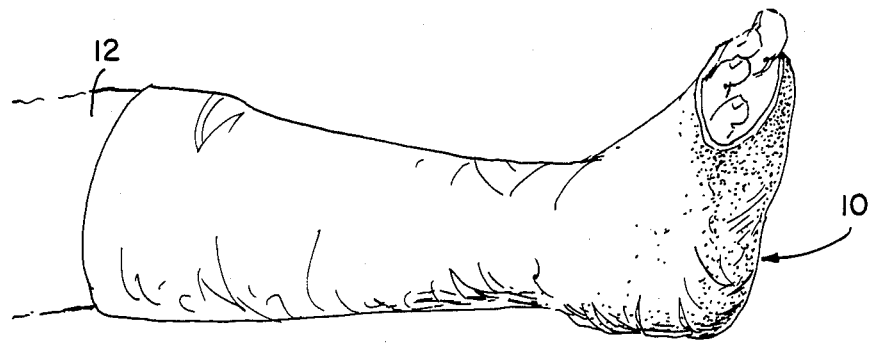
FIG. 1 illustrates one type of illustrative orthopedic cast which has been applied to a lower extremity of a patient's leg.

In this connection, FIG. 1 discloses an illustrative cast 10 which has been applied to lower extremity 12 of a patient. If the patient has undergone severe trauma, and there is soft tissue damage involved with the orthopedic fracture and/or strained ligaments, it is possible that the patient's limb may swell after the cast has been applied.

As discussed above, compartment syndrome may precipitate "Volkmann" disease and contractures. Contractures may ultimately result in the loss of function of the extremity as well as shortening and cosmetic deformities.

If the surgeon or physician detects swelling an obvious technique to relieve pressure on the limb would be to remove the cast structure entirely. Unfortunately, this concomitantly relieves orthopedic confinement which is necessary in order to immobilize the damaged bone and surrounding structure. In addition, the physical steps of removing and recasting requires physical manipulation which may create some mis-alignment and improper knitting and ultimate healing.

Alternatively, a longitudinal kerf may be cut into the cast structure to temporarily relieve swelling and pressure. Once swelling has subsided the cast can be manually re-closed and taped together to renew complete immobilization. The subject invention comprises a device to facilitate this latter technique of swelling management in a cast member.

Orthopedic Cast Spacing and Spreading Device

Figure 2:
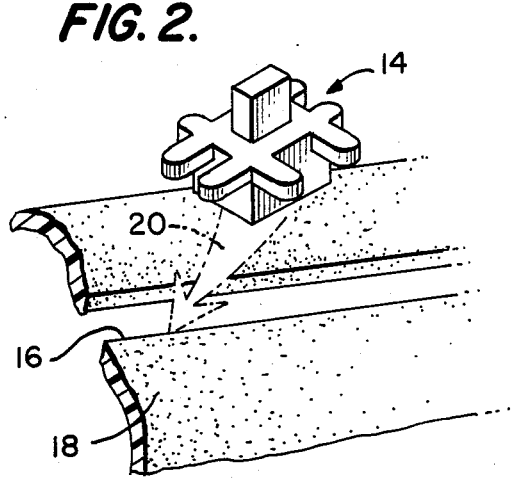
FIG. 2 is a schematic view of a longitudinal kerf formed within a patient's cast in the event of internal swelling and the intended insertion of an orthopedic cast spacing and spreading device in accordance with a preferred embodiment of the instant invention.
Figure 3:
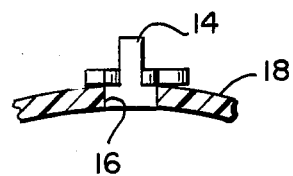
FIG. 3 is a detail cross-sectional view disclosing an orthopedic cast spacing and spreading device mounted within the kerf of a patient's cast to maintain the cast in a uniformly spread apart condition.
Figure 4:
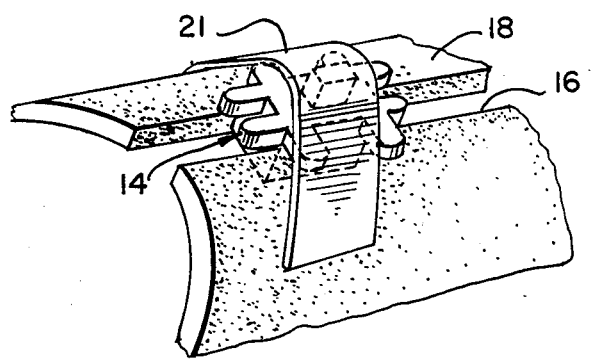
FIG. 4 discloses is an orthopedic cast spacing and spreading device positioned within the kerf of a spread apart cast and securely mounted and retained against undesired lateral travel by the application of an adhesive tape strip to secure the unit to the outer surface of the patient's cast.

Referring now particularly to FIGS. 2-4, there will be seen an orthopedic cast spacing and spreading device 14 which is operative to be inserted into a kerf 16 of a fiber glass resin type cast 18. As indicated above, when a kerf 16 is longitudinally cut within a resin cast 18 and spread apart by a spreading device of the type identified above internal pressure will be released, however, the resin material has a memory characteristic and upon removal of the spreading device or tool, the cast tends to return to an original configuration.

The subject orthopedic cast spacing and spreading device 14 may be operably inserted into a kerf as indicated by enlarged directional arrow 20 to a posture as depicted in the partial detail cross-sectional view in FIG. 3. The inside surfaces or edges of the cast 18, once released by cast spreading device will provide self gripping action upon lateral surfaces of a portion of the orthopedic cast spacing and spreading device as shown in FIG. 3.

In order to enhance secure positioning of the subject orthopedic cast spacing and spreading device, a patch of hospital adhesive tape 21 may be applied over the top of the orthopedic cast spacing and spreading device 14 to immobilize the device with respect to longitudinal travel within the kerf 16.

Figure 5:
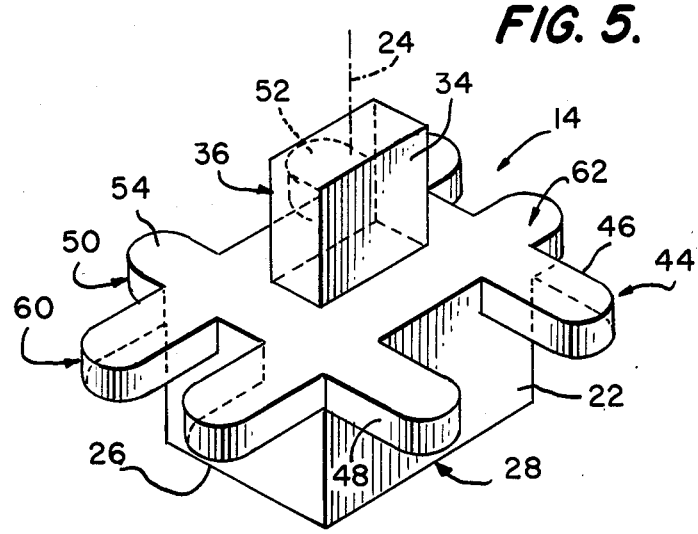
FIG. 5 is a detailed axonometric view of an orthopedic cast spacing and spreading device in accordance with a preferred embodiment of the subject invention.
Figure 6:
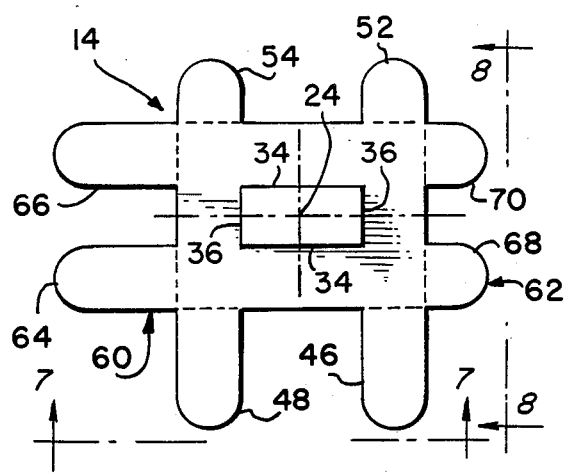
FIG. 6 is a plan view of the orthopedic cast spacing and spreading device as illustrated in FIG. 5.
Figure 8:
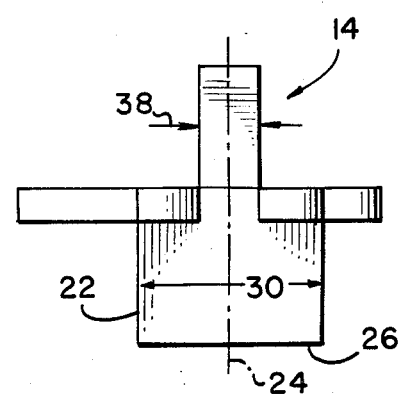
FIG. 8 is another side view of the cast spacing and spreading device depicted in FIG. 6 as viewed along directional arrows 8—8 in FIG. 6.
Figure 7:
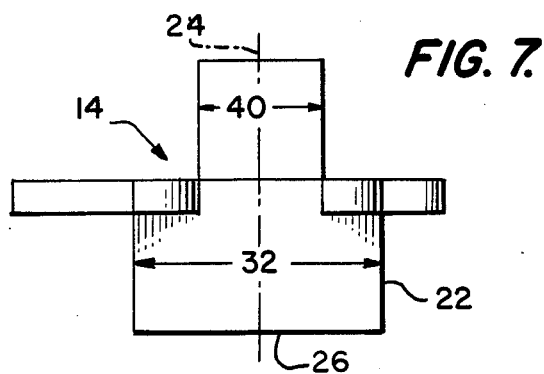
FIG. 7 is a side view of the orthopedic cast spacing and spreading device depicted in FIG. 6 as viewed along directional arrows 7—7 in FIG. 6.

Turning now to FIGS. 5-8, there will be seen detailed views of the orthopedic cast spacing and spreading device in accordance with the subject invention. Referring specifically to FIGS. 5, 7, and 8, there is disclosed a first orthogonal member 22 having a central longitunal axis 24 and end face 26 which is perpendicular to sidewall surfaces 28 of the first orthogonal member.

The sidewall surfaces 28 may assume a variety of cross-sectional configurations such as circular, elliptical, triangular, etc., but in a preferred embodiment, the sidewalls form, in cross-section, a rectangle. The first orthogonal member, as depicted in FIGS. 7 and 8, has opposing mutually parallel sidewall surfaces having a first width dimension 30 and a second, longer, length dimension 32.

The orthopedic cast spacing and spreading device 14 also includes a second orthogonal member 36 having one end face 34 which extends perpendicular to mutually parallel sidewall surfaces. The sidewall configuration, in a manner similar to that discussed in connection with the sidewall configuration of the first orthogonal member may be circular, elliptical, triangular, etc., but in a preferred embodiment is rectangular in cross-section. The rectangular sidewall surface 36 has a first width dimension 38 which is shorter than a length dimension 40. Moreover, the length dimension 40 of the second orthogonal member is less than the width dimension 30 of the first orthogonal member.

As shown in FIGS. 5-7, the central longitudinal axis 24 of the first orthogonal member 22 is preferably coincident with a central longitudinal axis of the second member 36 and said first and second orthogonal members are coaxially joined at the other ends thereof to form a unified member wherein the first end of faces of the first and second orthogonal members are mutually parallel and the first orthogonal member is coaxial with respect to the second. The first and second orthogonal members may be formed from structural elements but in a preferred embodiment are composed of solid rectangular members which exhibit a high degree of compression resistance.

A first lateral flange unit 44 projects laterally outwardly at the junction of the first and second orthogonal members and comprises a first arm 46 and a second arm 48. A second flange member 50 is mounted upon an opposing side of the first and second orthogonal members and includes a first arm 52 and a second arm 54. The first and second arms 46 and 48 extend in a posture mutually parallel and in alignment with mutually parallel second arms 52 and 54. As seen in FIG. 6, the arms 46 and 48 are longer than arms 52 and 54 with respect to the distance that they project outwardly from the junction location of the orthogonal members.

A second set of laterally projecting flanges 60 and 62 also are connected to and join with the first and second orthogonal members and project outwardly from opposing junction surfaces as shown in FIGS. 5 and 6. In a manner similar to the flanges 44 and 50, flanges 60 and 62 each comprise a pair of first and second arms 64 and 66 and 68 and 70 respectively. The laterally projecting arms 64 and 66 extend outwardly from the lateral surfaces of the orthogonal members a distance greater than the lateral extent of the arms 68 and 70.

The difference in the distance to which the lateral flanges extend ensures that there will be a lateral extent sufficient to rest upon an outer surface of a patient's cast adjacent to a kerf to prevent the orthopedic cast spacing and spreading device from falling into the kerf during application. Once inserted and the cast is self biased against lateral surfaces of the orthopedic cast spacing and spreading device. Additionally, a tape may be applied on top of the device as previously discussed in connection with FIG. 4 to laterally secure it in a fixed location and bind the cast together. The lateral extent of one side of the flange arms facilitates this securing operation.

It will appreciated by reference to the drawing that an orthopedic physician or surgeon utilizing the instant device may operably select one of four dimensions to be inserted into the cast depending upon the spacing required to be maintained to relieve pressure upon a swollen limb.

BRIEF SUMMARY OF MAJOR ADVANTAGES OF THE INVENTION

Without attempting to detail and enumerate all of the advantages specifically and inherently disclosed in the foregoing application specification, those skilled in the art will recognize several features which provide a enhanced degree of utility of the subject invention.

More specifically, the instant orthopedic cast spacing and spreading device is preferably composed of solid rectangular members which will when made of a generally incompressible plastic composition such as, polyvinyl chloride or polyurethane are relatively incompressible, and the four different dimensions provided by the solid rectangular members enables a physician to selectively utilize one of four dimensions when spacing a kerf in a previously applied cast.

The lateral projections of the subject orthopedic cast spacing and spreading device prevents the device from falling into the kerf and further provides a surface upon which to tape the device to an outer surface of a patient's cast to prevent motion of the device. Moreover, the projected flange arms ensures that the cast spacing and spreading device does not project too deeply within the kerf and thus come in contact with the patient's skin.

The subject cast spacing and spreading device may be economically molded and thus be widely utilized to uniformly provide spacing for a problem cast.

The plurality of opposing dimensions provided by the subject device ensures that one size may be utilized to meet the exigencies of varying spacing requirements.

In describing the invention, reference has been made to a preferred embodiment and illustrative advantages of the invention. Those skilled in the art, however, and familiar with the instant disclosure of the subject invention, may recognize additions, deletions, modifications, substitutions, and/or other changes which fall within the purview of the subject invention and claims.

We claim:

1. An orthopedic cast spacing and spreading device comprising:
   a first orthogonal member having,
      a generally planar first end face,
      a second end face, and
      mutually parallel side-wall surfaces extending between said end faces in a posture perpendicular to said first end face;
   a second orthogonal member having,
      a generally planar first end face,
      a second end face, and
      mutually parallel side wall surfaces extending between said end faces in a posture perpendicular to said first end face;
   said second end face of said first orthogonal member being joined to said second end face of said second orthogonal member;
   dimensions of said first orthogonal member transverse to a central longitudinal axis of said first orthogonal member being greater than dimensions of said second orthogonal member transverse to a central longitudinal axis of said second orthogonal member; and
   at least one flange connected to said orthopedic cast spacing and spreading device at the junction of said first and second orthogonal members and laterally projecting outwardly from said first and second orthogonal members, wherein a orthopedic physician may selectively insert said first or said second orthogonal member into a longitudinal kerf cut into a patient's orthopedic cast to spread and maintain the kerf in a uniformly spaced posture with the lateral flange operably resting upon an outer surface of the cast.

2. An orthopedic cast spacing and spreading device as defined in claim 1 wherein said first orthogonal member comprises:
   a generally rectangular member wherein opposing lateral sides have a width dimension and a longer, length dimension, wherein a physician may selectively insert either the width dimension or the second longer, length dimension between the inner kerf surfaces of the cast depending upon the longitudinal space desired to be maintained in the kerf.

3. An orthopedic cast spacing and spreading device as defined in claim 2 wherein said second orthogonal member comprises:
   a generally rectangular member wherein opposing lateral sides have a width dimension and a longer, length dimension and said width dimension of said first orthogonal member being greater than the length dimension of said second orthogonal member, wherein a physician may selectively insert any one of four dimensions between the inner kerf surfaces of the cast depending upon the longitudinal space desired to be maintained in the kerf.

4. An orthopedic cast spacing and spreading device as defined in claim 3 wherein:
said first and said second generally rectangular, orthogonal members are solid rectangular structures and stable against compression to securely maintain the kerf of a cast in a spaced condition.

5. An orthopedic cast spacing and spreading device as defined in claim 3 wherein said at least one flange comprises:
at least one member laterally projecting outwardly from each of said lateral surfaces of said rectangular members at the junction of said first and second generally rectangular members.

6. An orthopedic cast spacing and spreading device as defined in claim 5 wherein said at least one member comprises:
a pair of mutually parallel members laterally projecting outwardly from each lateral surface of said first and second generally rectangular members at the junction of said first and second rectangular members.

7. An orthopedic cast spacing and spreading device as defined in claim 6 wherein:
said pair of mutually parallel members on one side of the orthopedic cast spacing and spreading device extend outwardly a distance away from the lateral surface of the rectangular members greater than the distance the pair of mutually parallel members extend on the other side of the rectangular members.

8. An orthopedic cast spacing and spreading device as defined in claim 7 wherein:
said pair of mutually parallel members on one side of the orthopedic cast spacing and spreading device extend outwardly at least twice the distance away from the lateral surface of the rectangular members as on the opposing side of the orthopedic cast spacing and spreading device.

* * * * *